United States Patent [19]

Köhler et al.

[11] Patent Number: 5,786,440
[45] Date of Patent: Jul. 28, 1998

[54] MIXTURES OF CYCLIC OLIGOCARBONATES AND THEIR MANUFACTURE

[75] Inventors: Burkhard Köhler, Leverkusen; Duane B. Priddy, Jr., Krefeld; Yun Chen, Krefeld; Harald Pielartzik, Krefeld; Robert-Joseph Kumpf, Düsseldorf, all of Germany

[73] Assignees: Bayer Aktiengesellschaft, Leverkusen, Germany; Bayer Corporation, Pittsburgh, Pa.

[21] Appl. No.: 977,006

[22] Filed: Nov. 24, 1997

[30] Foreign Application Priority Data

Dec. 11, 1996 [DE] Germany .................. 196 51 445.2

[51] Int. Cl.⁶ .................................................. C08G 64/00
[52] U.S. Cl. .............................................. 528/196; 528/198
[58] Field of Search .................................. 528/196, 198

[56] References Cited

U.S. PATENT DOCUMENTS

| 4,755,586 | 7/1988 | Shannon et al. | 528/199 |
| 4,888,411 | 12/1989 | Shannon et al. | 528/199 |
| 4,972,039 | 11/1990 | Shannon et al. | 528/371 |

*Primary Examiner*—Terressa Mosley
*Attorney, Agent, or Firm*—Joseph C. Gil; Aron Preis

[57] ABSTRACT

A process for the manufacture of cyclic oligocarbonate is disclosed. The process comprises a reaction of a bis-chlorocarbonic acid ester with isatinbisphenol or with a bis-chlorocarbonic ester thereof. The mixture of cyclic oligocarbonates thus prepared is useful as a precursor in the preparation of modified polycarbonate or polyester resins.

7 Claims, No Drawings

MIXTURES OF CYCLIC OLIGOCARBONATES AND THEIR MANUFACTURE

The invention concerns a mixture of cyclic oligocarbonates and the process for its preparation. More specifically, the invention concerns a mixture of oligocarbonates which are obtained by reacting a bischlorocarbonic ester of bisphenol with isatinbisphenol.

Certain cyclic oligocarbonates have been disclosed in the art, see U.S. Pat. Nos. 4,755,586, 4,888,411 and 4,972,039.

It has now been found that a novel mixture of cyclic oligocarbonates may be manufactured by reacting a bischlorocarbonic ester of bisphenol with isatinbisphenol. The cyclic oligocarbonates of the present invention are suitable as precursors for the preparation of polycarbonate and polyesters.

Accordingly, the inventive mixture contains at least two members

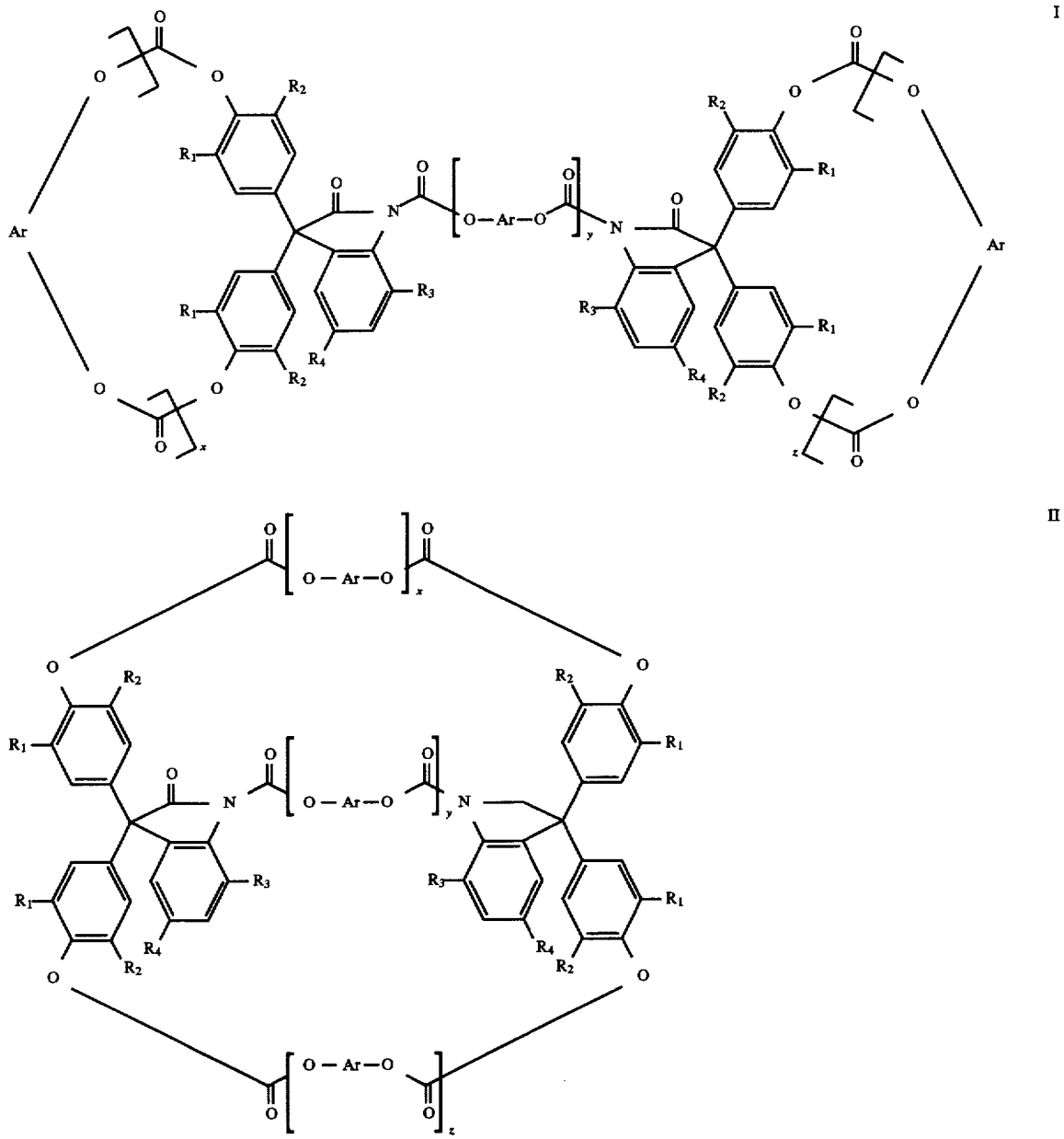

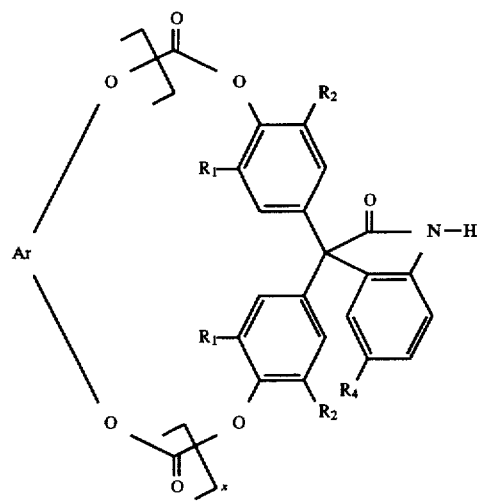

III

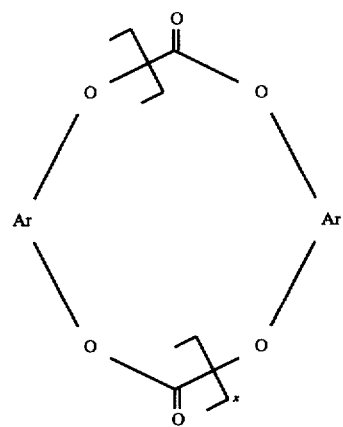

IV wherein $R_1$, $R_2$, $R_3$, and $R_4$ independently of each other denote hydrogen, halogen or $C_1$–$C_4$-alkyl, preferably hydrogen or methyl, Ar denotes a divalent aromatic residue, preferably a $C_{6-30}$-aromatic residue optionally containing —O—, —S— or —SO$_2$— units and further optionally containing chlorine and/or bromine substituents, and x, y and z independently one of the others denote integers of 0 to 20, preferably 1 to 8.

The inventive mixture may be prepared by the simultaneous introduction of at least one bis-chlorocarbonic ester of the formula

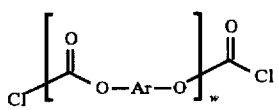

V whereby Ar has the above-mentioned meaning, and w is an integer of 1 to 4, and at least one isatinbisphenol conforming to

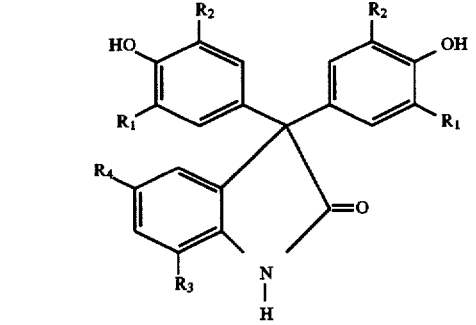

VI where $R_1$, $R_2$, $R_3$ and $R_4$ have the above-mentioned meaning, optionally along with at least one dihydroxy compound of the formula HO—Ar—OH, wherein —Ar— has the above-mentioned meaning, and a suitable catalyst into a two-phase mixture of an organic solvent and water at temperatures of 30° C. to 100° C., and where a solution or suspension of an alkali or alkali earth metal hydroxide is added to maintain a pH-value of 7 to 13, preferably 10 to 13.

The isatinbisphenol of formula VI may be used in the form of its bis-chlorocarbonic ester.

The bischlorocarbonic ester of the formula V suitable for the manufacture of the cyclic oligocarbonates may be prepared, for example, using the well known phase boundary process.

Preferred bisphenols conform to

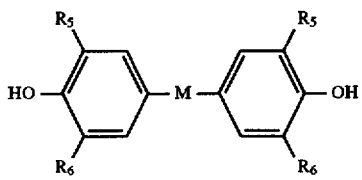    VII where $R_5$ and $R_6$ independently denote H, Cl, Br or $CH_3$—, and —M— is a single bond, —O—, —S—, —$SO_2$—, or the residue of $C_{1-5}$-alkylidene, $C_{2-6}$-alkylene, $C_{5-10}$-cycloalkylidene, benzylidene, phenethylidene or isophenethylidene, or the group

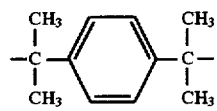

Examples of suitable bisphenols of the formula HO—Ar—OH include 4,4'-dihydroxydiphenyl; 2,2-bis-(4-hydroxyphenyl)-propane; 2,4-bis(4-hydroxyphenyl)-2-methylbutane; 1,1-bis(4-hydroxyphenyl)-cyclohexane; α,α-bis-(4-hydroxyphenyl)-p-diisopropylbenzene; 2,2-bis-(3-methyl-4-hydroxyphenyl)-propane; 2,2-bis-(3-chloro-4-hydroxyphenyl)-propane; bis-(3,5-dimethyl-4-hydroxyphenyl)-methane; 2,2-bis-(3,5-dimethyl-4-hydroxyphenyl)-propane; bis-(3,5-dimethyl-4-hydroxyphenyl)-sulfone; 2,4-bis-(3,5-dimethyl-4-hydroxyphenyl)-2-methylbutane; 1,1-bis-(3,5-dimethyl-4-hydroxyphenyl)-cyclohexane; α,α-bis-(3,5-dimethyl-4-hydroxyphenyl)-p-diisopropylbenzene; 2,2-bis-(3,5-dichloro-4-hydroxyphenyl)-propane and 2,2-bis-(3,5-dibromo-4-hydroxyphenyl)-propane and 1,1-bis(4-hydroxyphenyl)-3,3,5-trimethyl-cyclohexane, preferably 2,2-bis(4-hydroxyphenyl)-propane and 1,1-bis(4-hydroxyphenyl)-3,3,5-trimethylcyclohexane.

The mole ratio of the bisphenols conforming to HO—Ar—OH resulting from the reactant of formula V and the optionally added bisphenols, to the isatinbisphenols in the inventive mixture is about 99:1 to 85:15.

Solvents suitable in the inventive two-phase mixture with water are conventional organic solvents, for example, methylene chloride, chlorobenzene, o-dichloro-benzene, toluene, benzene, xylene, THF, dioxane, dioxolane, methyl-tert-butylether, diethylether, diisopropylether, dibutylether and dimethoxyethane.

In a preferred embodiment, a solution of the bischlorocarbonic ester of formula V in methylene chloride and/or chlorobenzene is first mixed with a solution of the isatinbisphenol of the formula VI in THF and/or dioxane and the mixture introduced, in the course of 10 to 60 minutes, preferably 30 minutes, into a reaction vessel simultaneously with the catalyst and the base.

The catalyst suitable in the process of the reaction is any of the known organic amine compounds known in the art, preferably tertiary amines. Among the more suitable catalysts, mention may be made of triethylamine and N-ethylpiperidine.

Examples for compounds of the formula VI include isatinbisphenol and isatinbis-o-cresol.

The cyclic oligocarbonates prepared in accordance with the process of the invention are well soluble in ethers, esters, or ketones, and may be applied as lacquers from these solutions. These may be cured at temperatures of 50° to 300° C., optionally, in the presence of suitable catalysts; such suitable catalysts include organic tin compounds, tetraalkylammonium tetraarylboranates, tetraalkylammoniumboranates, tetra-arylphosphoniumtetraarylboranates or tetracrylphosphonium-oranates.

The invention is further illustrated but is not intended to be limited by the following examples in which all parts and percentages are by weight unless otherwise specified.

EXAMPLES

Example 1

Preparation of bischlorocarbonic ester of 2,2-bis-(4-hydroxyphenyl)-propane (Bisphenol-A): reference Macromolecules 1991, 24, pages 3035–3044.

300 g phosgene is introduced over a period of 150 minutes to a mixture of 228 g (1 mol) bisphenol-A, 80 ml $H_2O$ and 1.2 liter $CH_2Cl_2$ at 0° C. Simultaneously, 25 weight % sodium hydroxide is added such that the pH of the mixture is maintained at 2 to 5. Approximately 1 liter of such sodium hydroxide solution is required for this. The pH value is then adjusted with the addition of more sodium hydroxide between 8–9 after the phosgene addition, and nitrogen is added until the solution is free of phosgene. After the phase separation, the organic phase is washed with 1N HCl and then with water, it is subsequently treated with anhydrous sodium sulfate and condensed. The yield was 218 g. The content of hydrolyzable chlorine was 16.5% (compare to theoretical value of 20.1%).

Example 2

Preparation of the inventive cyclic oligocarbonates. 200 ml $CH_2Cl_2$, 7 ml water and 3 ml of a 9.75 m NaOH are prepared and the solution of 63.58 g bischlorocarbonic ester from Example 1, and 6.9 g isatinbis-o-cresol in 200 ml $CH_2Cl_2$/THF 9:1, 59 ml 9.75 m NaOH and 2.4 ml triethylamine at 40° C. are simultaneously added under vigorous mixing and mixing is continued for 10 minutes. Hydrochloric acid is added, the phases are separated, and the organic phase is washed 3 times with water. Cyclic oligocarbonate (43 g) was separated by centrifugation. The cyclic oligocarbonates are free of phenolic OH-end groups, according to the UV analysis. The molecular weight (determined by GPC, RI-detector) was Mn=3118 g/mol and Mw=7774 g/mol.

Example 3

Manufacture of bischlorocarbonic ester from 1,1-bis(4-hydroxyphenyl)-3,3,5-trimethylcyclohexane (Bisphenol-TMC).

300 g phosgene are introduced to a mixture of 310 g (1 mol) bisphenol-TMC, 80 ml $H_2O$ and 1.2 liter $CH_2Cl_2$ at 0° C. over 150 minutes. At the same time, a 25 weight % sodium hydroxide is dosed in such a way that the pH-value of the mixture is between 2 and 5. Approx. 1 liter of sodium hydroxide is required for this. The pH-value is adjusted between 8–9 after the phosgene introduction and nitrogen is supplied until the solution is phosgene-free. After the phase separation, the organic phase is washed with 1N HCl and then with water, is subsequently washed over sodium sulfate and condensed. The yield was 327 g. The content of hydrolyzable chlorine was 13.4% compared to the value of 16.3% of the pure bischlorocarbonic ester of the bisphenol-TMC.

Example 4

200 ml $CH_2Cl_2$, 7 ml water, and 3 ml of a 9.75 m NaOH is prepared and the solution of 78.3 g bischlorocarbonic ester from Example 3 and 6.9 g isatinbis-o-cresol in 200 ml $CH_2Cl_2$/THF 9:1, 59 ml 9.75 m NaOH and 2.4 ml triethylamine are simultaneously added at 40° C. under vigorous mixing and mixing is continued for 10 minutes. Hydrochloric acid is added. the phases are separated and the organic phase is washed 3 times with water. After centrifuging, 29 g cyclic oligocarbonate was obtained. The cyclic oligocarbonates are free of phenolic OH-end groups according to the UV analysis. The molecular mass (determined by GPC, RI-detector) was Mn=2480 g/mol and Mw=7375 g/mol.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the manufacture of cyclic oligocarbonate comprising a reaction of (a) bis-chlorocarbonic acid ester of the formula

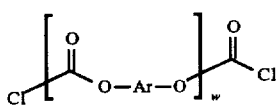

V where Ar is a $C_{6-30}$-difunctional aromatic residue of a dihydroxy compound and w is an integer of 1 to 4, with (b) isatinbisphenols of the formula

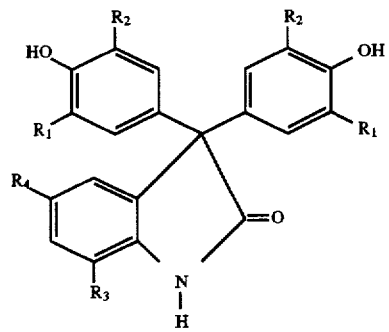

VI or with a bis-chlorocarbonic ester of said isatinbisphenol, where $R_1$, $R_2$, $R_3$, and $R_4$ independently denote hydrogen, halogen or a $C_{1-4}$-alkyl group.

2. The process of claim 1 wherein said reaction further comprise a dihydroxy compound conforming to the formula HO—Ar—OH.

3. A mixture comprising at least two compounds selected from the group consisting of compounds conforming to formula

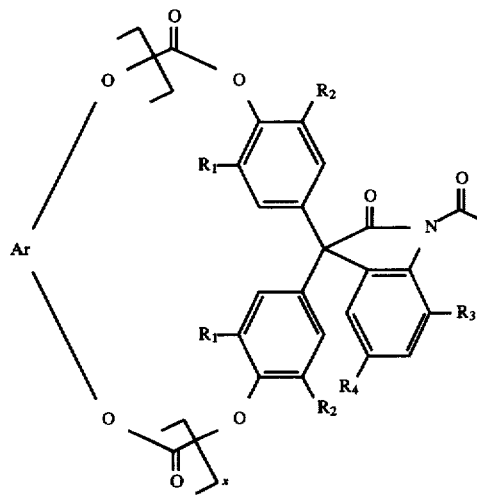
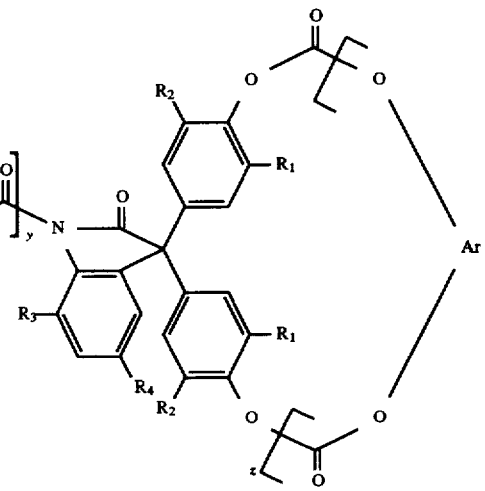

I

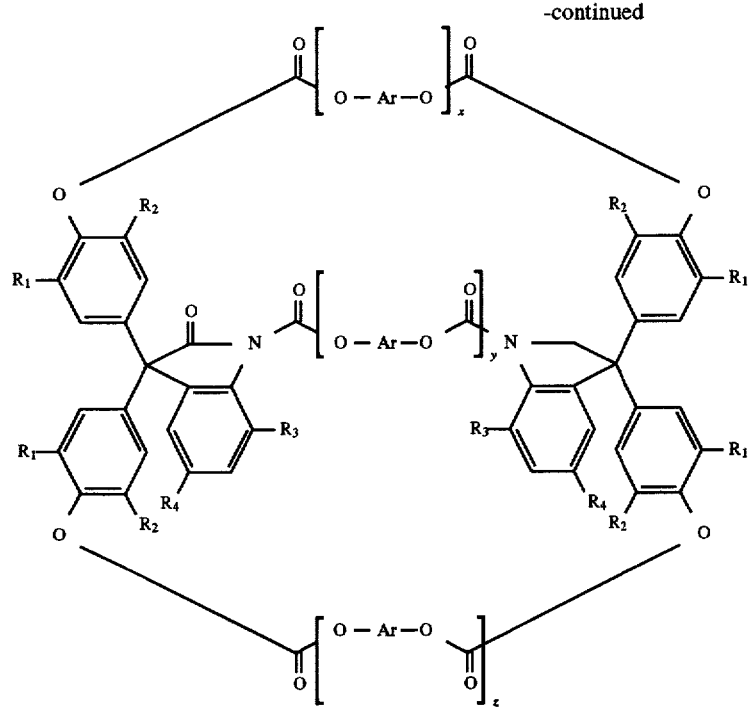
II
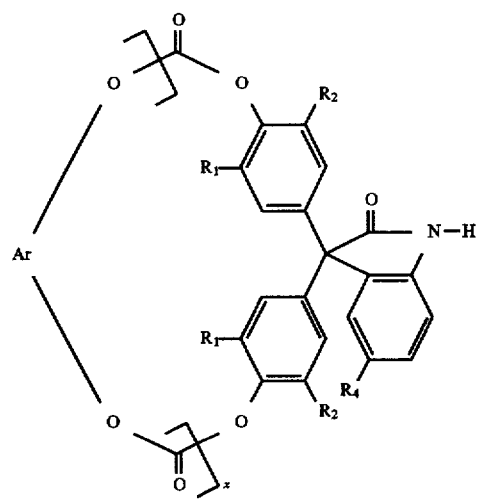
III
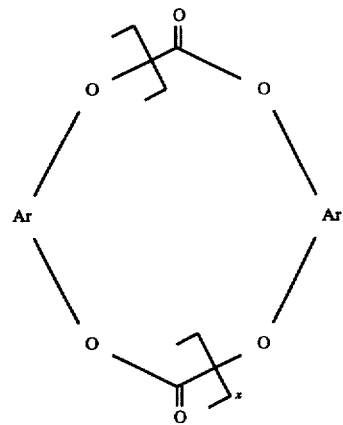
IV
wherein x, y and z independently one of the others denote integers of 0 to 20, prepared by the process of claim 1.
4. The mixture of claim 3 wherein $R_1$, $R_2$, $R_3$, and $R_4$ independently denote hydrogen, or a methyl group.

5. The process of claim 1 wherein said Ar containing a member selected from the group consisting of —O—, —S— and —SO$_2$—.

6. The process of claim 1 wherein said Ar contain chlorine and/or bromine substituents.

7. The mixture of claim 3 wherein x, y and z independently one of the others denote 1 to 8.

* * * * *